United States Patent [19]
Kraus et al.

[11] Patent Number: 5,290,241
[45] Date of Patent: Mar. 1, 1994

[54] RAPID REMOVAL OVER-THE-WIRE CATHETER

[75] Inventors: Jeffrey L. Kraus, San Jose; Joseph R. Shields, Sunnyvale; Nitin P. Matani, San Jose, all of Calif.

[73] Assignee: Danforth Biomedical, Incorporated, Menlo Park, Calif.

[21] Appl. No.: 962,150

[22] Filed: Oct. 16, 1992

[51] Int. Cl.⁵ .................................. A61M 5/178
[52] U.S. Cl. ......................... 604/161; 604/158; 604/284
[58] Field of Search ............... 604/49, 158, 160, 161, 604/164, 264, 280, 284, 283

[56] References Cited

U.S. PATENT DOCUMENTS

| | | | |
|---|---|---|---|
| 4,687,469 | 8/1987 | Osypka | 604/161 |
| 4,743,265 | 5/1988 | Whitehouse et al. | 604/161 |
| 4,748,982 | 6/1988 | Horzewski et al. | 128/344 |
| B1 4,762,129 | 7/1991 | Bonzel | 606/194 |
| 4,762,129 | 7/1988 | Bonzel | 128/344 |
| 4,883,468 | 11/1989 | Kousai et al. | 604/161 |
| 4,887,997 | 12/1989 | Okada | 604/161 |
| 4,988,356 | 1/1991 | Crittenden et al. | 606/192 |
| 4,997,424 | 3/1991 | Little | 604/161 |
| 5,040,548 | 8/1991 | Yock | 128/898 |

FOREIGN PATENT DOCUMENTS

| | | |
|---|---|---|
| 0282143 | 1/1988 | European Pat. Off. |
| 0380873 | 12/1989 | European Pat. Off. |

*Primary Examiner*—John G. Weiss
*Attorney, Agent, or Firm*—David H. Jaffer

[57] ABSTRACT

The present invention is an "over-the-wire" catheter having a proximal adapter system which may be used to open a longitudinally closed guidewire lumen, thereby facilitating rapid removal of the catheter without a guidewire extension mechanism.

16 Claims, 1 Drawing Sheet

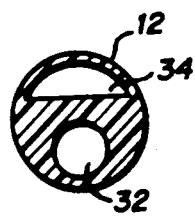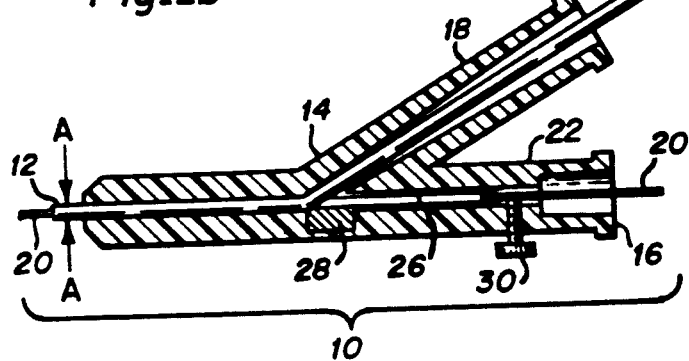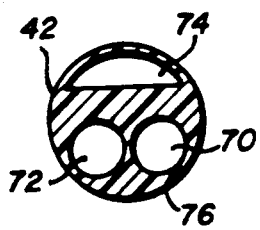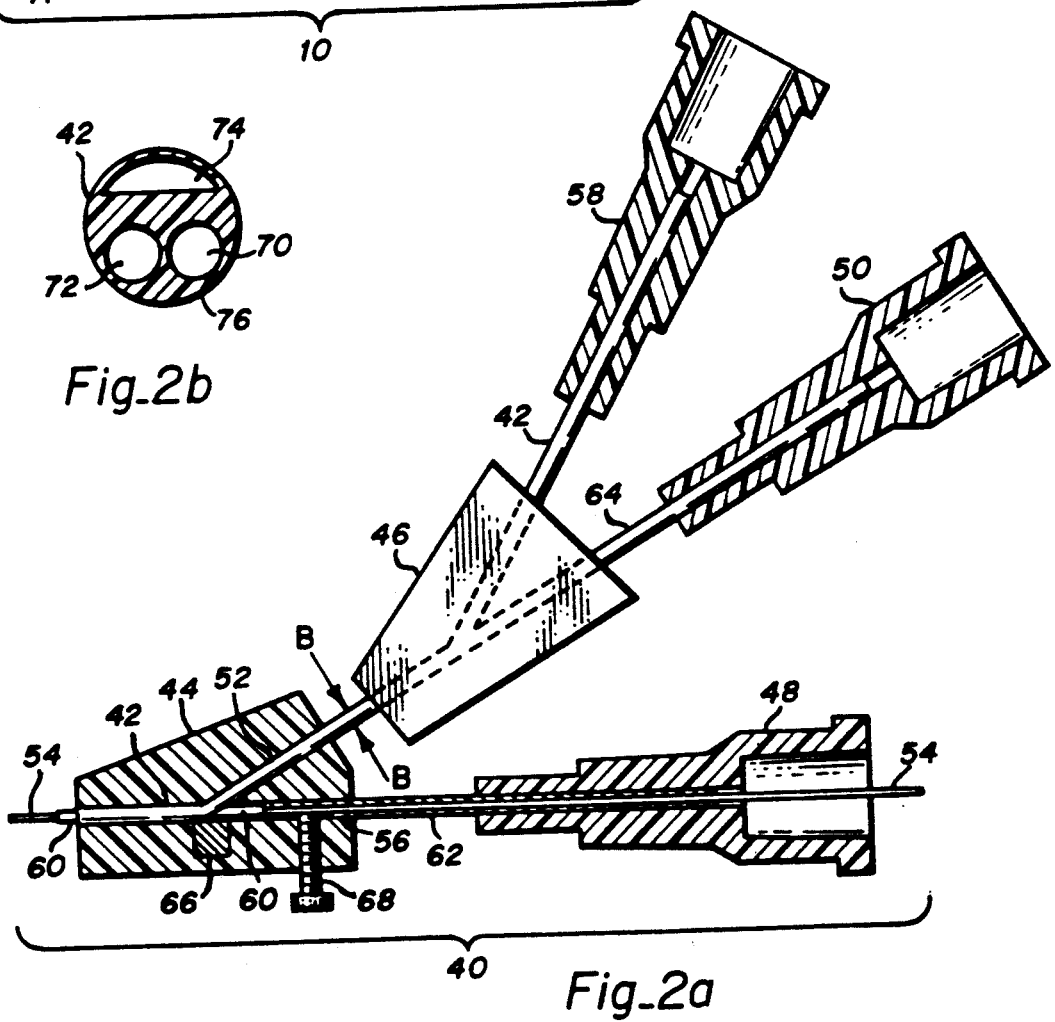

RAPID REMOVAL OVER-THE-WIRE CATHETER

BACKGROUND OF THE INVENTION

1. Field of the Invention

This invention relates generally to an over-the-wire catheter, and more particularly to an over-the-wire catheter which may be simply and rapidly removed while a guidewire remains in place without use of an exchange wire or extension mechanism.

2. Brief Description of the Prior Art

Various configurations of catheters and guidewires have been developed over the years for the purpose of satisfying different functional requirements. "Over-the-wire" catheter systems permit full rotational and full coaxial mobility of the guidewire relative to the catheter component of the system. "Over-the-wire" catheters can be fully withdrawn over a guidewire, and they will accept the antegrade and retrograde introduction of a guidewire therethrough. U.S. Pat. No. 4,323,071 describes an "over-the-wire" system.

While "over-the-wire" systems allow for removal of catheters along a fixed guidewire, such removal is mechanically difficult because "over-the-wire" systems require that an exchange wire or other extension mechanism protrude from the patient's body by a length greater than the length of the catheter. Thus, manipulation of the catheter and guidewire during catheter removal is complicated.

A different type of catheter-guidewire system has been developed to address this problem. Known generically as "rapid exchange" or "monorail" catheters, the design permits catheter removal over a standard 175 cm length guidewire. U.S. Pat. Nos. 4,762,129 to Bonzel, 4,748,982 to Horzewski et al., and 5,040,548 to Yock teach variations of such designs. The designs include an inflation lumen within the catheter which runs the length of the catheter, and a separate guidewire lumen which extends a relatively short distance from the distal end toward the proximal end of the catheter. Horzewski et al. describe use of a slit in the guidewire lumen to further reduce the closed length of the guidewire lumen. Since the guidewire lumen is relatively short compared to the overall length of the catheter, when a catheter is withdrawn over the guidewire and replaced with another guidewire, a guidewire extension is not required.

The "monorail" concept has been readily accepted because it permits simple and rapid catheter removal. However, a major problem of the design is that once a "monorail" catheter has been positioned, the guidewire is extremely difficult to exchange. This is because the guidewire lumen is relatively short. When the catheter is in place and the guidewire is withdrawn, it is impractical to locate the guidewire lumen with a replacement guidewire while the "monorail" catheter (and entrance to the guidewire lumen) is within a patient's body.

Crittenden et al., U.S. Patent No. 4,988,356, have addressed this problem with a catheter system including a guidewire lumen which is slit longitudinally along the length of the catheter and a guide member which serves to spread the slit of the guidewire lumen to guide the guidewire into or out of the slit lumen. The system acts in zipper-like fashion over the length of the catheter.

SUMMARY OF THE INVENTION

It is a primary objective of the present invention to provide an "over-the-wire" catheter design which allows guidewires to be exchanged while the catheter is in place, and which may be simply and rapidly removed without an exchange wire or extension mechanism by opening the guidewire lumen.

Another object of the present invention is to provide an "over-the-wire" catheter design in which the guidewire lumen may be opened for rapid removal of the catheter from the guidewire, while also providing a guidewire lumen with sound structural integrity. Maintenance of such integrity is of particular importance in low-profile catheters, where the diameter of the catheter is as small as structurally possible.

Still another object of the present invention is to provide an "over-the-wire" catheter design with multiple guidewire lumens, each of which may be opened to permit rapid removal of the catheter after each guidewire lumen is used, thereby permitting separate insertions of the catheter using the multiple guidewire lumens.

A further object of the present invention is to provide a catheter core member which enhances shaft rigidity and facilitates guidewire loading when the multiple guidewire lumen catheter is used.

Briefly, the preferred embodiment of the present invention comprises an "over-the-wire" catheter having a longitudinally closed guidewire lumen which extends from near the proximal end to near the distal end of the catheter. The invention provides means for opening the guidewire lumen, thereby facilitating rapid removal of the catheter Without an exchange wire or extension mechanism. The guidewire lumen is opened with a slitting device preferably positioned on the proximal adapter of the catheter. The catheter has the advantages of an "over-the-wire" catheter for guidewire replacement and the rapid removal capability of a "monorail" catheter, while also retaining the structural integrity inherent in a longitudinally closed guidewire lumen.

The objects above and other objects and advantages of the present invention will no doubt become apparent to those skilled in the art after having read the following detailed description of the preferred embodiment which is contained in and illustrated by the various drawing figures.

IN THE DRAWINGS

FIG. 1(a) is a cross-sectional view of the proximal portion of a catheter in accordance with the preferred embodiment of this invention, taken along the lengthwise axis of the catheter;

FIG. 1 (b) is a cross-sectional view of the device shown in FIG. 1(a) with the guidewire removed, taken along line A—A of FIG. 1(a);

FIG. 2(a) is a cross-sectional view of the proximal portion of the multiple guidewire lumen embodiment of this invention, taken along the lengthwise axis of the device; and FIG. 2(b) is a cross-sectional view of the device shown in FIG. 2(a) taken along line B—B of FIG. 2(a).

DETAILED DESCRIPTION OF THE PREFERRED EMBODIMENT

This invention relates to an "over-the-wire" catheter design which allows guidewires to be exchanged while the catheter is in place, and which may be simply and rapidly removed without an exchange wire or extension mechanism by opening the guidewire lumen. The guidewire lumen is opened with a slitting device, preferably positioned on the proximal adapter of the catheter. The catheter may be provided with multiple guidewire lumens, each of which may be opened to permit rapid removal of the catheter after use of that guidewire lumen. This permits multiple insertions of the catheter with the separate guidewire lumens.

Referring now to FIG. 1(a) of the drawing, proximal adapter system 10 is shown. Proximal adapter system 10 includes catheter tubing 12, proximal adapter 14, and an inflation/deflation fitting 24. Catheter tubing 12 is a multi-lumen catheter, such as a dilatation catheter. As shown in FIG. 1(b), the walls of catheter tubing 12 define an inflation lumen 34 and a guidewire lumen 32. The cross-section shown in FIG. 1(b) is taken along line A—A of FIG. 1(a), with the guidewire 20 and tubular member 26 not shown for the sake of simplicity. The remainder of the catheter beyond the proximal adapter system 10 shown in FIG. 1(a) is a standard multi-lumen catheter as known in the prior art. Note that while this invention is described with reference to a multi-lumen catheter, it is equally applicable to single lumen or coaxial catheters.

Proximal adapter 14, which is preferably formed of a rigid plastic material, contains a single passageway at its distal end which divides into two passageways, one passageway in first arm 18 and a second passageway in second arm 22 of proximal adapter 14. As FIG. 1(a) shows, catheter tubing 12 extends through the passageway in the distal side of the proximal adapter 14, through first arm 18, to inflation/deflation fitting 24 (which is preferably a Luer-type fitting).

A passage is provided in second arm 22 of proximal adapter 14 for guidewire 20. Second arm 22 terminates in a Luer fitting 16 for guidewire 20.

On the distal side of proximal adapter 14, guidewire 20 is encompassed within catheter tubing 12. In particular, guidewire 20 is within guidewire lumen 32 (see FIG. 1(b)). At the junction of the first arm 18 and second arm 22 of proximal adapter 14, catheter tubing 12 is separated from guidewire 20. This separation is facilitated by the use of slitting device 28. Slitting device 28 splits guidewire lumen 3 to allow separation of catheter tubing 12 from guidewire 20 o the proximal side of the slitting device. On the distal side of slitting device 28, guidewire lumen 32 is not split and is closed to the exterior of the catheter.

Slitting device 28 is preferably a razor edge. In the preferred embodiment the razor is metal, but any sharpened rigid object may also be used. In addition, slitting device 28 may be a relatively blunt surface if catheter tubing 12 is formed of plastic materials which have a compositional discontinuity in the region when catheter tubing 12 contacts slitting device 28. For example, catheter tubing 12 may be composed of plastics of different composition, with the non-compatible plastics meeting in the region between guidewire lumen 32 and the outer wall of catheter tubing 12. This creates a weak point or a weld line. When this portion of the catheter tubing 12 contacts slitting device 28, catheter tubing 12 opens along the compositional discontinuity, thereby opening guidewire lumen 32.

FIG. 1(a) shows that guidewire 20 extends beyond Luer fitting 16 on second arm 22 of proximal adapter 14. Guidewire 20 is preferably guided into catheter tubing 12 through tubular member 26 which has a smooth transition to allow easy insertion of the guidewire. Tubular member 26 extends from second arm 22 through the distal end of proximal adapter 14, preferably terminating in approximately the region of line A—A in FIG. 1. Tubular member 26 may be formed of hypodermic tubing, and provides an entry for guidewire 20 into catheter tubing 12 which is fixed to proximal adapter 14. Tubular member 26 may either be bonded or molded in place. Guidewire gripper 30 is provided in second arm 22 of proximal adapter 14 to ensure that guidewire 20 may be retained in a fixed position with respect to proximal adapter 14 when catheter tubing 12 is moved relative to proximal adapter 14.

Proximal adapter system 10 is assembled and used in the following manner. Guidewire lumen 32 of catheter tubing 12 is inserted from the distal side of proximal adapter 14 over tubular member 26 (which extends to approximately the region of line A—A in FIG. 1). At this point, guidewire lumen 32 is split, and catheter tubing 12 is passed into first arm 18. Inflation lumen 34 is sealed to inflation/deflation fitting 24. Inflation/deflation fitting 24 is releasably secured to first arm 18. In FIG. 1(a), inflation/deflation fitting 24 has been released from first arm 18. Luer fitting 16 on second arm 22 is attached to tubular member 26 so that a guidewire may be loaded into Luer fitting 16 and on into guidewire lumen 32. Guidewire gripper 30 is recessed enough so as to not interfere with the loading of the guidewire.

Upon assembly of the catheter device, catheter tubing 12 and guidewire 20 are inserted into the patient's body. Should it become necessary to exchange guidewire 20 while the catheter tubing 12 is in place in the patient's body, guidewire 20 is extracted and a substitute guidewire inserted. Similarly, catheter tubing 12 may be removed and reinserted in the standard over-the-wire manner with the use of a guidewire extension mechanism or exchange wire.

When rapid removal of catheter tubing 12 without a guidewire extension mechanism or exchange length wire is desired, while retaining guidewire 20 in place, slitting device 28 is used. Guidewire gripper 30 is locked upon guidewire 20, to maintain guidewire 20 in place with respect to proximal adapter 14. If gripper 30 is not provided, the guidewire may be held by the operator. Slitting device 28 may be permanently mounted in contact with catheter tubing 12, or may be movably mounted so that it may be moved to engage catheter tubing 12 when rapid removal of catheter tubing 12 is desired. When slitting device 28 is in contact with catheter tubing 12, pulling the catheter tubing in a proximal direction (i.e. out of the patient's body), while holding proximal adapter 14 and guidewire 20 in position in the patient's vasculature causes catheter tubing 12 to be pulled across slitting device 28, opening guidewire lumen 32. In the preferred embodiment, Luer fitting 24 is released from proximal adapter 14 and used to pull catheter tubing 12. In FIG. 1(a), Luer fitting 24 has been released and catheter tubing 12 partially pulled across slitting device 28. Thus, catheter tubing 12 is separated from guidewire 20, which remains in a stationery position. When catheter tubing 12 has been slit nearly to the distal end of the catheter, guidewire gripper 30 may be released, permitting proximal adapter 14 and catheter tubing 12 to be removed from guidewire 20.

Once catheter tubing 12 and proximal adapter 14 have been removed while retaining guidewire 20 in place, new catheter tubing may be inserted. This may either be a monorail-type catheter inserted over the guidewire without a guidewire extension, or a standard over-the-wire catheter, in which case a guidewire extension must be used for reinsertion of the replacement catheter tubing.

As discussed above, slitting device 28 permits rapid removal of an over-the-wire catheter without having to use a guidewire extension. In addition, the use of catheter tubing 12 with a closed guidewire lumen on the distal side of slitting device 28 retains advantages of an over-the-wire catheter which are not retained with a guidewire lumen that is split from distal to proximal end of the catheter tubing. In particular, if catheter tubing 12 is split from proximal to distal end, guidewire 20 may not be retained within guidewire lumen 32 if the catheter and guidewire meet difficult bends when guided into place. Such bends may cause the guidewire to exit the guidewire lumen in a catheter where the guidewire lumen is split. This consideration is of particular importance as catheters are designed for smaller and smaller profiles (cross-sections). Since smaller profiles demand thinner catheter walls, it becomes increasingly difficult to seal a slitted guidewire lumen dependably and ensure that the guidewire remains within the slitted guidewire lumen.

With reference to FIG. 2(a), a multiple guidewire lumen embodiment of this invention is shown. Proximal adapter system 40 includes catheter tubing 42, first proximal adapter 44, second proximal adapter 46, inflation/deflation Luer fitting 58, first guidewire Luer fitting 48, and second guidewire Luer fitting 50.

As in the embodiment shown in FIGS. 1(a) and 1(b), catheter tubing 42 in FIGS. 2(a) and 2(b) is a multilumen catheter, in this case with multiple guidewire lumens 70 and 72, and inflation lumen 74. FIG. 2(b) shows a cross-section taken along line B—B of FIG. 2(a), in which first guidewire lumen 70 is open with slit 76 because first guidewire lumen 70 has been pulled across slitting device 66.

Second proximal adapter 46 is merely shown in outline as it is similar to proximal adapter 14 shown in FIG. 1(a) or first proximal adapter 44 shown in FIG. 2(a), except that (as shown in FIG. 2(a)) a guidewire has not yet been threaded through second guidewire lumen 72. Inflation/deflation fitting 58 is connected to second proximal adapter 46 with catheter tubing 42. This portion of the device may also be reinforced with rigid plastic, if desired, surrounding catheter tubing 42. Second guidewire Luer fitting 50 is attached to second proximal adapter 46 with second fitting extension 64, which is also preferably composed of a rigid plastic.

The use of first proximal adapter 44 is essentially the same as that of proximal adapter 14 described above with reference to FIG. 1(a). First proximal adapter 44 has a single passageway at its distal end which divides into two passageways, one in first arm 52 of proximal adapter 44, and a second in second arm 56 of proximal adapter 44. Catheter tubing 42 extends through the passageway in the distal side of first proximal adapter 44, through first arm 52 to second proximal adapter 46. The passage in second arm 56 of proximal adapter 44 is provided for guidewire 54. Second arm 56 is connected with first fitting extension 62 to first guidewire Luer fitting 48.

On the distal side of first proximal adapter 44, guidewire 54 is encompassed Within catheter tubing 44. (Catheter tubing 42 is cut away in FIG. 2(a).) Guidewire 54 is within first guidewire lumen 70. At the junction of first arm 52 and second arm 56 of proximal adapter 44, catheter tubing 42 is separated from guidewire 54 with slitting device 66. Slitting device 66 splits first guidewire lumen 70 to allow separation of catheter tubing 42 from guidewire 54 on the proximal side of slitting device 66. Thus, on the distal side of slitting device 66 guidewire lumen 70 is closed to the exterior of the catheter, but on the proximal side of slitting device 66 guidewire lumen 70 is opened through slit 76 created by slitting device 66.

As in the embodiment shown in FIG. 1 (a), a guidewire gripper 68 is provided in second arm 56 of first proximal adapter 44. In addition, tubular member 60 extends from second arm 56 of proximal adapter 44 through the distal end of proximal adapter 44, providing an entry for guidewire 54 into catheter tubing 42.

In this multiple guidewire configuration, a stiffening mandrel, preferably composed of stainless steel, is preferably inserted in the guidewire lumen which is not being used for the guidewire. The stiffening mandrel which would preferably be inserted in second guidewire lumen 72 is omitted from the drawing for the sake of simplicity.

In a case in which first proximal adapter 44 is used with guidewire 54 and guidewire lumen 70, a stiffening mandrel would be used in guidewire lumen 72 to add stiffness to the catheter and to prevent guidewire 54 from entering the wrong guidewire lumen if the guidewire is backloaded. In the case of reuse of the catheter with second guidewire lumen 72 after first guidewire lumen 70 has been split, a stiffening mandrel may be inserted into first guidewire lumen 70 to facilitate backloading of guidewire 54 into second guidewire lumen 72 and to provide additional stiffness to the catheter when it is reinserted.

The embodiment shown in FIG. 2(a) is used in a manner similar to the embodiment shown in FIG. 1 (a). When rapid removal of catheter tubing 42 without a guidewire extension mechanism is desired, while retaining guidewire 54 in place, slitting device 66 is used. Guidewire gripper 68 is locked upon guidewire 54 to maintain guidewire 54 in place with respect to first proximal adapter 44. When catheter tubing 42 is pulled in a proximal direction across slitting device 66, first guidewire lumen 70 is opened, creating slit 76. Catheter tubing 42 is thereby separated from guidewire 54. When catheter tubing 42 has been slit nearly to the distal end of the catheter, guidewire gripper 68 may be released, permitting first proximal adapter 44 to be removed from guidewire 54. This releases all of proximal adapter system 40 from guidewire 54, while guidewire 54 is retained in place.

Catheter tubing 42 still has second guidewire lumen 72 which is closed (not slit) from proximal to distal end. If reinsertion of the catheter is required, a guidewire extension may be attached to guidewire 54, and catheter tubing 42 reinserted using second guidewire lumen 72. Second proximal adapter 46 may be designed for use in a standard "over-the-wire" catheter configuration, or may be used for rapid removal by separation of guidewire 54 from second guidewire lumen 72 in the same manner that proximal adapter 14 was used as described with reference to FIG. 1. When second proximal adapter 46 is used, first proximal adapter 44 may be positioned near the proximal end of catheter tubing 42 or may be removed. If a stiffening mandrel is desired, first proximal adapter 44 may be repositioned near the proximal end of catheter tubing 42 by pulling catheter tubing 42 in a distal direction. Now a stiffening mandrel may be inserted into first guidewire lumen 70 (which is now split but still will adequately retain the mandrel), and catheter tubing 42 is backloaded into second guidewire lumen 72.

An alternative multi-lumen embodiment utilizes a longitudinally closed first guidewire lumen and proximal adapter with means for opening the first lumen as described above, and a second guidewire lumen of the "rapid exchange" or "monorail" type. Thus, the catheter may be initially utilized as an over-the-wire catheter, rapidly removed with the catheter-proximal adapter system described above, and then reinserted without a guidewire extension or exchange wire through use of the "monorail" guidewire lumen. Of course, this procedure can be reversed, with the "monorail" guidewire lumen used first and the longitudinally closed guidewire lumen used second. In this case, the catheter can be converted to an over-the-wire catheter that may be rapidly removed without a guidewire extension or exchange wire if necessary.

Although the present invention has been described in terms of specific embodiments, it is anticipated that alterations and modifications thereof will no doubt become apparent to those skilled in the art. It is therefore intended that the following claims be interpreted as covering all such alterations and modifications as fall within the true spirit and scope of the invention.

What is claimed is:

1. An over-the-wire catheter system adapted for rapid removal, comprising:
   (a) catheter tubing having a plurality of lumens that extend from near the distal end of the catheter tubing to near the proximal end of the catheter tubing, the lumens being longitudinally closed from near their distal ends to near their proximal ends, at least one of said plurality of lumens being a guidewire lumen;
   (b) a guidewire inserted in the guidewire lumen; and
   (c) opening means for opening the guidewire lumen situated near the proximal end of the guidewire lumen, thereby permitting the catheter tubing to be separated from the guidewire while retaining the guidewire in place.

2. The catheter system of claim 1, wherein the opening means is disposed in a proximal adapter attached to the catheter tubing.

3. The catheter system of claim 2, wherein the proximal adapter comprises a first passageway at the distal end of the proximal adapter which branches to a passageway for the guidewire and a passageway for the catheter tubing, and said opening means is situated in the first passageway, thereby facilitating separation of the guidewire and the catheter tubing after the guidewire lumen has been opened by the opening means.

4. The catheter system of claim 3, further comprising a tubular member extending from the passageway for the guidewire in the proximal adapter to the distal side of the opening means, thereby providing means for insertion of the guidewire into the guidewire lumen.

5. The catheter system of claim 1, further comprising a second guidewire lumen, thereby permitting use of the catheter tubing with a guidewire inserted in the second guidewire lumen after the first guidewire lumen has been opened.

6. The catheter system of claim 5, further comprising a core member inserted into the guidewire lumen that is not used for the guidewire, thereby providing enhanced pushability to the catheter.

7. The catheter system of claim 1, wherein the catheter tubing comprises non-compatible materials meeting in the region between the guidewire lumen and the outer wall of the catheter tubing, forming a weak point that opens upon contact with the opening means.

8. A proximal adapter for use with an over-the-wire catheter having a guidewire and catheter tubing with a longitudinally closed guidewire lumen in which the guidewire may be positioned, comprising:
   (a) a first passageway for positioning the catheter tubing and the guidewire in the proximal adapter;
   (b) opening means disposed in the proximal adapter for opening the guidewire lumen as the catheter tubing is moved in a proximal direction with respect t the proximal adapter and the guidewire;
   (c) a second passageway for the guidewire and a third passageway for the catheter tubing, said second and third passageways branching from the first passageway on the proximal side of the opening means, thereby facilitating separation of the guidewire and the catheter tubing after the guidewire lumen has been opened by the opening means; and
   (d) a fourth passageway for the guidewire and a fifth passageway for the catheter tubing, said fourth and fifth passageways branching from the proximal end of the third passageway, whereby a second guidewire lumen in the catheter tubing may be separated from the guidewire upon reinsertion of the catheter tubing over the guidewire utilizing the second guidewire lumen after the first guidewire lumen has been opened.

9. The proximal adapter of claim 8, further comprising second opening means disposed in the third passageway for opening the second guidewire lumen as the catheter tubing is moved in a proximal direction with respect to the proximal adapter and the guidewire, whereby the catheter tubing may be separated from the guidewire while the guidewire is retained in place.

10. A method for removing an over-the-wire catheter while retaining a guidewire in position, comprising:
   (a) loading the guidewire into catheter tubing having a guidewire lumen, said lumen being one of a plurality of lumens that extend from near the distal end of the catheter tubing to near the proximal end of the catheter tubing, the lumens being longitudinally closed from near their distal ends to near their proximal ends;
   (b) positioning the catheter in a patient's vasculature;
   (c) separating the catheter tubing from the guidewire by moving the catheter tubing in a proximal direction while retaining the guidewire in place, causing the catheter tubing to move across opening means situated near the proximal end of the guidewire lumen, thereby opening the guidewire lumen and permitting the catheter tubing to be separated from the guidewire; and
   (d) removing the catheter tubing from the guidewire while retaining the guidewire in position for further use of said guidewire.

11. The method of claim 10, further comprising the step of attaching the catheter tubing to a proximal adapter in which the opening means is disposed, and wherein the step of removing the catheter tubing from the guidewire comprises releasing the proximal adapter from the guidewire.

12. The method of claim 11, wherein the proximal adapter comprises a first passageway at the distal end of the proximal adapter which branches to a second passageway for the guidewire and a third passageway for the catheter tubing, said opening means is situated in the first passageway, and wherein the step of attaching the catheter tubing to the proximal adapter comprises directing the catheter tubing into the third passageway, whereby as the catheter tubing in moved in a proximal direction the guidewire lumen of the catheter tubing is opened by the opening means and the catheter tubing moves through the third passageway of the proximal adapter.

13. The method of claim 12, wherein the proximal adapter further comprises a tubular member extending from the second passageway to the distal side of the opening means, and the step of loading the guidewire comprises insertion of the guidewire through the tubular member into the unopened portion of the guidewire lumen.

14. A method for use of a catheter comprising the steps of claim 10, and further comprising the step of reinserting the catheter in the patient's vasculature over a guidewire through a second guidewire lumen in the catheter tubing.

15. The method of claim 14, further comprising the step of inserting a core member into the guidewire lumen that is not used for the guidewire, thereby providing enhanced pushability to the catheter.

16. The method of claim 10, wherein the catheter tubing comprises non-compatible materials meeting in the region between the guidewire lumen and the outer wall of the catheter tubing, forming a weak point that opens upon contact with the opening means.

* * * * *